United States Patent [19]

Helmer et al.

[11] Patent Number: 5,680,321
[45] Date of Patent: Oct. 21, 1997

[54] METHOD OF QUANTIFYING THE PROPERTIES OF PAPER

[75] Inventors: Ulla Helmer, Solna; Lars Renberg, Västerhaninge; Ralf Olsson, Stockholm, all of Sweden

[73] Assignee: Eka Nobel AB, Bohus, Sweden

[21] Appl. No.: 443,667

[22] Filed: May 18, 1995

[30] Foreign Application Priority Data

May 18, 1994 [SE] Sweden ................... 9401718

[51] Int. Cl.$^6$ ................................................ G06F 19/00
[52] U.S. Cl. ................................ 364/499; 364/471.03
[58] Field of Search ................................. 364/499, 498, 364/497, 496, 471, 469.01, 469.02, 471.01, 471.02, 471.03; 162/49, 198; 210/745, 143

[56] References Cited

U.S. PATENT DOCUMENTS

| | | |
|---|---|---|
| 5,104,485 | 4/1992 | Weyer . |
| 5,121,337 | 6/1992 | Brown . |
| 5,206,701 | 4/1993 | Taylor et al. . |
| 5,242,602 | 9/1993 | Richardson et al. . |
| 5,446,681 | 8/1995 | Gethner et al. ................ 364/554 |

OTHER PUBLICATIONS

S.D. Brown, "Chemometrics", Anal. Chem. 62, pp. 84R–101R (1990).

Pulp characterization using spectroscopy and multi–variate data analysis, L. Wallbäcks, Dept. of Organic Chemistry, Univ. of Umeå, Sweden (1991).

Abstract of Research Disclosure 344066 by Hercules Incorporated.

*Primary Examiner*—Emanuel T. Voeltz
*Assistant Examiner*—M. Kemper
*Attorney, Agent, or Firm*—Burns, Doane, Swecker & Mathis, L.L.P.

[57] ABSTRACT

A method for the quantification of the one or several of the physical properties selected from dry tensile strength, hydrophobicity, debonding energy, bursting strength, wettability and printability of pulp and/or paper which method comprises (I) developing a calibration model by
 (I.a) registering absorption, reflectance or emission spectra of reference samples of paper of known properties as defined above to develop learning sets;
 (I.b) processing the spectral raw data, to reduce noise and adjust for drift and diffuse light scatter;
 (I.c) performing a data analysis by applying chemometric techniques to the processed learning sets; and (II) determining the unknown properties as defined above of pulp and/or paper by registering the absorption, reflectance or emission spectrum, in correspondence to (I.a), from the pulp and/or paper having unknown properties; processing the thereby obtained spectral raw data as according to (I.b); and applying the developed calibration model to the processed data.

Optionally, a data analysis step as according to (I.c) can also be applied to the processed spectral raw data from the paper having unknown properties.

28 Claims, 6 Drawing Sheets

METHOD OF QUANTIFYING THE PROPERTIES OF PAPER

FIELD OF THE INVENTION

The properties of pulp and paper treated with performance chemicals cannot today be quantified in the paper machine but must be tested off-line at the paper mill. Said procedures are drawbacks to the productivity and the economy of the paper production process.

The present invention is directed to a method for the quantification of the physical properties of pulp and paper treated with paper chemicals and more particularly to a method for quantifying the properties of paper containing, e.g. wet and dry strength agents, starches and retention agents; hydrophobic (sizing) agents, such as alkyl ketene dimer (AKD), alkylene succinic anhydride (ASA), carbamoylchloride and rosin; and debonding agents (fluff chemicals) such as e.g. quaternary fatty amines and fatty amine oxides. Properties to be determined are e.g. dry tensile strength, hydrophobicity, debonding energy, bursting strength, wettability and printability.

However, it is not sufficient only to know or determine the amounts of added or retained chemicals to predict the properties as there are often no apparent connections between the amounts of performance chemicals as added and the values of the properties as obtained. The resistance of a given paper or board to the sorption of water is e.g. a function not only of the surface characteristics of the fibers achieved by the presence of a sizing agent, but is also dependent on the structure of the web (i.e. the size of pores, its density, the surface treatments to which it has been subjected, etc.). (Cf. J. C. Roberts, Paper chemistry, Blackie Academic & Professional, Glasgow, 1992, p 97).

BACKGROUND OF THE INVENTION

For a number of paper applications the physical properties as mentioned above are of fundamental importance, examples being that of papers of tissue quality, as well as paper bags and paper sacks, printing qualities and paper board.

The Technical Association of Pulp and Paper Industries (TAPPI) and Scandinavian Pulp, Paper and Board Testing Committee (SCAN) define the testing methods for properties in pulp and paper.

One major drawback with those methods of quantifying the properties is the delay between a change in a parameter at the manufacturing of a paper and the answer of the determination of the property. This delay may lead to important losses in case the properties prove to be inadequate since, by the time this assessment has been accomplished, there may be very large quantities of paper of these inadequate properties produced.

It is obvious that the methods of testing these properties presently in use in the paper production industry are drawbacks to the productivity and the economy of the paper production process. Thus, there is a definite need for a more convenient method of testing the properties in the paper manufacturing industry.

The present invention has for object to offer a solution to said problem, by providing a method that allows the quantifying of said properties of the paper and pulp during the production process. This object is attained by the combined use of spectrometric and chemometric techniques.

According to the invention, the paper or the pulp in or off the production line is submitted to spectrometric analysis. However, the pulp as well as the paper represents a multi-component system or a system having a high degree of background interferences which increases the problem of spectrometric analysis.

The use of multivariate data analysis in the characterization of multi-component systems is presently a field of development. Applied generally to the field of chemistry, and particularly to the field of analytical chemistry, those several statistical methods also are termed chemometric methods, forming the discipline of chemometrics. The technique of chemometrics is more fully explained in S. D. Brown, "Chemometrics", Anal. Chem. 62, 84R–101R (1990), which by reference is incorporated herein in its entirety.

An example of the use of chemometrics is given in the thesis of Wallbäcks (Pulp characterization using spectroscopy and multivariate data analysis, L. Wallbäcks, Dept. of Organic Chemistry, Univ. of Umeå, Sweden (1991)), who has shown that multivariate data analysis can be used to predict various physical properties as a function of the initial characteristics of the unbeaten pulp and the effect of beating.

Further, Brown et al, in the U.S. Pat. No. 5,121,337 (1990) disclose a method, based on multivariate data analysis, for correcting spectral data for data due to the spectral measurement process itself and estimating unknown property and/or composition data of a sample using such method.

On the other hand, Richardson et al, in U.S. Pat. No. 5,242,602 disclose a method for simultaneously measuring the concentration of multiple chemical components, which they call performance indicators, in an aqueous system, by the analysis of the spectrum of the aqueous system in the wavelength range 200 to 2500 nm and by applying chemometric algorithms to the spectrum to simultaneously determine the concentrations of the different performance indicators.

Weyer, U.S. Pat. No. 5,104,485 discloses a method for measuring extremely low concentrations of non-aqueous constituents or chemicals in a water/matrix, including differentiating between pulp fines and extremely low concentrations of individual chemicals in a water/cellulose matrix such as occur in papermaking. The water/matrix is exposed to the near-infrared spectrum from 1000 to 2500 nm to produce a record voltage that is directly proportional to the absorption by the non-aqueous constituent. The amount non-aqueous constituent is determined from voltage values of incremental additions of the non-aqueous constituent.

In addition Hercules reported in a research disclosure (December 1992/945) that in the papermaking process, a water/cellulose mixture is laid on a wire screen and the water is filtered off leaving the fibers and various additives. The paper sheet produced is composed of cellulose fibers, fillers such as clay ad calcium carbonate, and additives such as optical brighteners, sizes, and wet and dry strength resins. Various instrumental systems are available for measuring some of these constituents such as the clay. These systems, however, are limited in the determinations that can be carried out. A method for determining several individual chemical constituents simultaneously in a paper sheet has been developed according to Hercules. Radiation from a near infrared source is allowed to impinge upon the paper sheet, and after interaction of the radiation with the chemical constituents in the sheet, the reflected radiation is collected and stored. The chemical composition is calculated from the stored data after mathematical treatments are applied. The measurement system is calibrated via samples of known composition. Use of the full near infrared spectrum from 1100 to 2500 nanometers permits the analysis of several constituents simultaneously, especially when derivatives are employed as part of the mathematical treatment. This analysis aids in determining the extent of retention of the chemical additives and fillers.

However, the present inventors have shown that four steps should be involved for a useful quantification of a chemical on the basis of spectroscopy. The first step is recording the simultaneously determination of the emission, transmittance or reflectance values from a huge number of wave lengths (e.g. 300 to 600 numbers of wave length is not uncommon). The second step is a pre-treatment of the spectral data, which is essential in the NIR region (800–2400 nm). The third step is transformation of data, usually by centering, normalization or autoscaling the data. The fourth step is to find the mathematical expression for the calibration function.

The description of the method according to Hercules only disclose the first and second step. The spectral information is collected, followed by an undefined mathematical treatment. The only detail that is given is the application of derivatives (which is a commonly used technique within spectroscopy). Nothing is revealed about the numerical algorithm used for the transformation of data and algorithm for calibration. This step is of utmost importance for a useful quantification of a chemical on the basis of spectroscopy.

However, according to this invention specific algorithms are applied to overcome especially two disadvantages, namely:

1. The number of wave lengths can be considerable and outnumbers the number of samples, used for the calibration. As an example, if the reflectance of 300 wavelength are recorded for 20 samples, with conventional mathematical models only the values from the number of samples minus 2 can be used for the calibration. Thus, in this case only values from 20−2=18 wave lengths can be used and the information from the other 282 wave lengths cannot be taken into account. According to this invention all spectral information is used and compiled by transferring all the information recorded into so called latent variables based on principal component analysis.

2. The spectral information is often highly correlated which seriously affect the success for quantification. If the spectral information is transferred into latent variables by principal component analysis a higher degree of orthogonalisation is obtained which can be a crucial factor for success.

Moreover, none of the above mentioned authors suggests how to solve the problem of determining the effect of the chemicals present in a paper or the properties of paper, in a paper production process in a way permitting the monitoring of these parameters and no details of the calibration procedures are given. It should be emphazised that the expression "determination" in this context can be interpreted either as a qualitative analysis or as a quantitative analysis. A qualitative analysis is the determination of the presence of a chemical or a property while quantitative analysis relates to the estimation of a certain value, including the degree of uncertainty of this value (expressed in statistical terms such as confidence interval etc.). The object of the present invention is to provide a reliable and precise way of monitoring— i.e quantification—the effect of chemicals present in a paper by spectroscopic measurement in combination with multivariate data analysis using chemometrical techniques.

The object of the invention thus is to provide a method of determination of the above-mentioned properties of pulp and paper treated with performance chemicals in real time without the use of the traditional lengthy mechanical measurements and analytical methods.

It is another object of the invention to provide a method of maintaining an effective process control program wherein the above-mentioned properties are quantified to detect any change and provide control input, assuring optimum dosage levels for the different chemical additives.

The methods and means as disclosed according to the invention are those as further defined in the claims.

The invention relates to the determination of properties in paper, specifically tensile strength, hydrophobicity, debonding energy, bursting strength, wettability and printability.

Pulp and paper obtain strength from the interfibrillar hydrogen bonds which are created when the cellulose fibers are drawn together by surface tension during the drying process. Certain chemical additives, such as starch, improve the dry strength of a paper by creating a large contact area between the fibers in the paper.

Dry defibration of cellulose pulp gives a cotton like soft material, fluff, used in absorbing sanitary products such as diapers etc. The pulp product intended for use for dry defibration has to be treated with debonding agents in some cases containing both hydrophobic and hydrophilic groups. The hydrophilic group will increase the absorption speed and capacity in the final product and counteract the hydrophobicity rendered by the hydrophobic groups.

The interfibrillar hydrogen bonds should be as few as possible in the pulp intended for fluff. The most common debonding agents are quaternary fatty amines. The big hydrophobic groups interfere with and prevent the formation of hydrogen bonds.

The fluff pulp is produced on a paper machine as a thick paper and the debonding agents are added to the stock as ordinary paper chemicals. There has to be no destruction of the fibers during the defibration process and the energy needed to defibrate the fibers in a fluff pulp should be as low as possible. The bursting strength is a good measurement of the debonding energy needed for good defibration of the pulp/paper.

The definition of bursting strength is: the highest pressure applied on paper without any breakage in the paper. The unit for this strength is $N/m^2=Pa$. For paper the multiple unit 1000 Pa=kPa is used. This property can also be given as burst index: Bursting strength divided by the grammage weight with the unit $kPa*m^2/g$. Testing of bursting strength and burst index is today performed according to SCAN P 24:77 Scandinavian Pulp, Paper and Board Testing Committee as follows: The paper sample is placed and fixed on a circular rubber membrane. Underneath this membrane a fluid is pumped until the paper bursts. The pressure of the liquid when the burst occur is the bursting pressure.

For fluff pulp evaluation, standardized fiberizing of the pulp sample is of outmost importance. Such evaluations are presently made in pin-fiberizer e.g. as developed by Stora Corporate Research Center. By this method the debonding energy is determined for the pulp, intended for fluff.

Another important property for fluff is the wettability which is measured as time of absorption: The time in seconds it takes to completely saturate a test sample with absorbed water is standardized according to SCAN-C 33:80.

The test procedure is as follows: A specific sample of fluff is prepared according to standard in the shape of a cylinder of 3 gram with the diameter of 50 mm. This sample is then placed vertically on a net in a low beaker and a weight of 500 gram is placed on top of the sample. Water is added to the beaker and the sample absorbs water from below, the time needed for the penetration of water to the upper surface of the sample is measured and is reported as absorption time.

Yet another property important for paper or board is hydrophobicity city commonly achieved by sizing. Internal sizing is the process of imparting hydrophobicity to the paper by adding the chemicals at the wet end. Said process is carried out to produce paper or board that has an enhanced resistance to penetration by liquids such as water and printing inks. According to J. M. Gess in Paper Chemistry by J. C. Roberts, Blackie Academic & Professional, p. 97–113, the meaning of the term sizing depends on whether or not one is referring to the resistance of the sheet of paper or board to the sorption of water, or to the water resistance of the cellulose fibers. The distinction is extremely important, because the resistance of a given paper to the sorption of water is a function not only of the surface characteristics of the fibers achieved by the presence of a sizing agent but it is also dependent on the structure of the web, i.e. the size of the pores, its density, the surface treatments to which it has been subjected, etc. It also depends on the properties of the test fluid being used to measure sizing and the test procedure itself.

Many other factors influence the degree to which paper or paper-board will resist penetration by liquids as well. These may include the amount of and type of sizing agent retained in the paper, pH, drying conditions etc. Sizing is achieved by different mechanisms and by a variety of chemicals. Rosin in different formulations is the most commonly used internal sizing agent. There are different ways to produce the rosin acids from softwood. Current economics favour tall oil as a source. Tall oil rosin is obtained by distillation of acidified black liquor from the kraft pulping of soft wood. The main components are the so called rosin acids, all tricyclic acids. Abietic acid and levo pimaric acid are very important and have one carboxyl group each. The carboxyl group plays an important role for the development of sizing with rosin as they form ionic bonds with cationic aluminum ions (stemming from aluminum sulphate, paper makers alum). Good hydrophobicity is not achieved by the rosin itself but by the aluminum rosinates. The rosin particles have a size from 0,05 to 1 µm depending on the formulation. They are retained on the fines or fibers by ionic bonds. To increase the possibilities to form aluminum rosinates the levo pimaric acid is modified with a maleic anhydride or fumaric acid which gives a reaction product with three carboxyl groups the so called fortified rosin.

Many wet end factors effect sizing with rosin such as pH, alum level, type of rosin formulation, type of fibers, degree of refining, stock temperature, solved substances, defoamers etc. Many of them have an impact on the formation of the ionic bond, the alum bridge to cellulose. If the internal pH of the fibre is high during the paper production in a low pH surrounding, this bridge will be destroyed by time, the paper will lose its hydrophobicity and the sizing becomes fugitive. If a rosin sized paper is exposed to acidic solutions (milk, juice, ink etc.) the bridge, the ionic bond, will be destroyed and the hydrophobicity will disappear.

The second mechanism for sizing is the chemical anchoring of single molecules containing fatty alkyl groups on the cellulose surface. The most common cellulose reactive product is the alkyl ketene dimer, the AKD, added to the stock as dispersions and retained by heterocoagulation of the cationic size particle and the negatively charged surface of the fines or the coarse fibers. The dispersed droplets break in the drying section of the paper machine and AKD is more or less spread over the surface and can react with the hydroxyl groups. They form a direct covalent linkage with cellulose via β-keto ester. Those esterbonds are less sensitive to acidic conditions than rosin and AKD is used in liquid boards exposed to milk,juice etc. The bonds can be destroyed by fresh precipitated calcium carbonate (PCC) containing hydroxyl ions used as fillers in many paper qualities. This destruction of the ester bonds can be a rather slow process. The sizing is fugitive and the hydrophobicity will decrease. The alkenyl succinic acid anhydride (ASA), the alkyl carbamoyl chloride (DACC) and the alkyl isocyanate (SIC) are like AKD able to undergo reaction with the cellulose.

The third mechanism is achieved by different wax sizes. The paraffin melts and covers the surface and the paper or board gets a hydrophobic surface. The wax emulsions are stabilized in different ways. The soap stabilized emulsions are often alum precipitated and the soaps (the wax droplets) will be anchored to the surface as rosin and the wax itself is physically adsorbed.

The hydrophobicity "sizing" of the paper is tested according to the Cobb test designed to estimate resistance to absorption of water and further described in SCAN-P 12:64 (1964). The Cobb number indicates the quantity water taken up by one $m^2$ of paper during a certain time period.

Hercules Sizing Tester, HST, is widely used for quality control and measures the change in reflectance of paper as ink or a colored solution penetrates from the other side. In the HST test the liquid is contained in a ring on top of the paper, and the change in reflectance is measured photoelectrically from the bottom. For routine quality control, a convenient end point is chosen, for example, a reduction in reflected light of 20%. (See TAPPI, T530 pm-89.)

Printability of ink-jet print refers to the quality of the image produced. Important parameters measured are the black text optical density, the wicking of black ink into the fibers, the optical density of composite black print composed of the three primary colors, and the bleed of composite black print into a colored printed background. Colored bleed is further separated into line growth which is a measure of overall increase in the width of the line, an edge roughness which considers protrusions out of the main body of the line into the adjacent background color.

Optical density is measured using a reflective optical densitometer in which the density depends on the thickness of the ink layer.

Black wicking and color bleed are measured using image analysis by grabbing the image and measuring the area of a defined part of the text or the printed pattern. An increase in area indicates an increase in wicking or bleeding.

The above outlined situations illustrate the fact that the paper manufacturing process with short process times require continuous quantifying and control. This necessitates rapid repetitive testing with subsequent manual control adjustments, or continuous automatic testing with dynamic control adjustments wherein sensors are coupled directly to computer controllers which are capable of metering chemical feed pumps, mechanical milling devices, etc.

SUMMARY OF THE INVENTION

The above objects of the invention are obtained by a method of determination of one or several of the physical properties selected from dry tensile strength, hydrophobicity, debonding energy, bursting strength, wettability and printability in paper by analyzing the visible, near-infrared and/or infrared spectrum of the paper/pulp in the process line in a wavelength range within 200 nm to 400 µm, preferably 800 nm to 2500 nm and applying chemometric evaluation of the spectrum to calculate the physical properties of the paper.

DETAILED DESCRIPTION OF THE INVENTION

Figure 1:
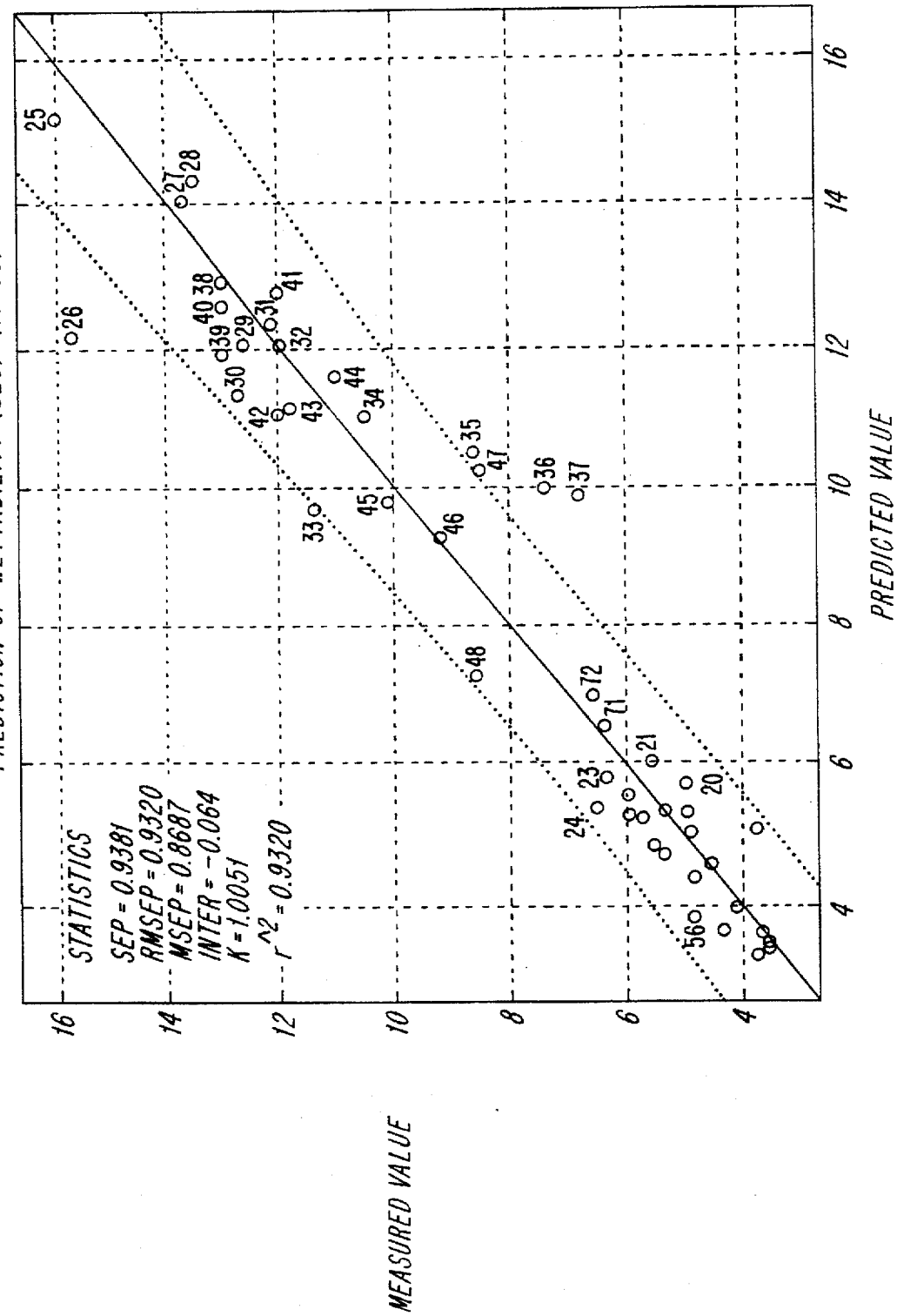
FIG. 1 represents the measured vs. predicted values of wettability in seconds of 60 samples of paper.

According to the invention it has now, by an extensive development work, been shown that it is possible to record the absorption, reflectance and emission spectra of pulp and paper using a UV-VIS-NIR and/or IR spectrometer and, by the use of absorbance, reflectance or transmittance values at discrete wavelengths from these spectra, calculate the above defined parameters of the corresponding paper.

The terminology pulp and/or paper as used herein refers not only to bleached pulp and/or paper, but also to unbleached or partially bleached pulp and/or paper as well as filled or unfilled qualities. This includes sac paper, liner, liquid board, printing paper and the like as well as creped paper qualities.

Technically, the spectrometric analysis can be performed by on-line, in-line, at-line or off-line measurement and can be carried out as a monitoring, by use of an on-line, in-line or at-line probe, or by taking individual samples for separate analysis (off-line). In both cases, the emission, transmittance or reflectance spectra are subject to further data treatment using values from several discrete wavelengths from each particular spectrum.

An example of such a technique is the use of a device, placed at a distance from the process, containing a light source, detector, electronic components and other necessary components to transmit a signal through an optical fibre to the sample, where the light is transmitted through or reflected on or partly through the sample. The resulting signals are returned to the detector in an accompanying optical fiber cable, and recorded.

In the spectrometer, the light is converted into an electric signal which is then conveyed to a computer where the spectrum of a previously stored reference scan can be related to, e.g. subtracted from, the sample spectrum and a reference corrected spectrum is calculated.

Another example is by manually or automatically taking samples at relevant time intervals and submitting the samples to analysis in an analytical instrument, containing the light source, detector, electronic components and other necessary components. The emission, transmittance or reflectance spectra are then subjected to further data treatment, using values from several discrete wavelengths from each particular spectrum.

The detection is performed in the UV-VIS-NIR wavelength range of 200 nm to 2500 nm, preferably 800 nm to 2500 nm and/or the IR wavelength range of 2500 nm to 400 µm. This can be accomplished by the use of a scanning instrument, a diode array instrument, a Fourier transform instrument or any other similar equipment, known to the man skilled in the art.

It is preferred that the detector have a measuring interval of at least 10 nm, preferably 2 nm, and most preferably 1 nm or less.

An evaluation of wavelengths which contain absorption, reflectance or emission provides features relevant for the analyses. By way of the application of chemometrical methods to the obtained spectra it is then possible to ignore wavelengths which do not contain relevant information, even though the measurement will include information from the entire wavelength range.

The determination and control of the physical properties as defined above in pulp and/or paper by use of the spectrometric measurements comprise three main sequences, the first main sequence being the development of a calibration model, involving the sequence of development of learning sets; data processing; and data analysis, by use of pulp and/or paper samples of known properties; and the second main sequence being that of the spectrometric analysis of the sample of the unknown properties of spectral data processing, optionally followed by data analysis; and application of the calibration model, developed in the first main sequence, to the thereby obtained data.

(I) DEVELOPMENT OF A CALIBRATION MODEL

The desired properties are measured in the traditional way (according to TAPPI and SCAN) for a number of pulp and/or paper samples. These samples, characterized by traditionally measured property values then are used in the development of a calibration model wherein the three sequences mentioned above are applied to the registered absorption, reflectance or emission spectra of said samples.

(I.a) Development of Learning Sets

Model learning sets consist of a large number of absorption, reflectance or emission spectra from the samples with known property characteristics, which samples preferably should be representative of the production line. The learning sets are used in the chemometric algorithms to calculate the resulting model parameters.

(I.b) Data Processing

To reduce noise and adjust for base line drift the spectral raw data should be processed. This processing may also reveal hidden information, such as identity of apparently dissimilar spectra or non-identity of apparently very similar spectra.

Moreover, the assumptions leading to Beer's law (stating that, for a given absorption coefficient and length of the optical path in the absorptive media, the total amount of light absorbed is proportional to the molecular concentration of the sample) are usually not fulfilled in the complex system that constitutes the pulp or paper. This is mostly due to light scatter variation depending on the physical dimensions of the sample.

Various theories have been developed to overcome this problem and the most used are:

1) The Kubelka-Munk transform (P. Kubelka, F. Munk, Z. Tech. Physik 12, 593 (1931)), which takes account of absorption and scatter, is according to Eq. 1:

$$A_{ik} = \frac{(1-R_{ik})^2}{2R_{ik}} \quad (1)$$

where $R_{ik}$ is the apparent absorbance at the wavelength k, $A_{ik}$ is the transformed absorbance at the wavelength k, and the index i represents the sample spectra available.

2) The Multiplicative Scatter Correction (MSC) (P. Geladi, D. MacDougall, H. Martens, Appl. Spect. 39, 491–500 (1985)) where each spectrum is 'corrected' in both offset and slope by comparing it to an 'ideal' spectrum (the mean spectrum), is according to Eq. 2:

$$A_{ik} = \frac{R_{ik} - \hat{a}_i}{\hat{b}_i} \quad (2)$$

where $A_{ik}$, $R_{ik}$, i and k have the same meanings as above, $\hat{a}_i$ is the least squares estimation of the intercept parameter, and $\hat{b}_i$ is the least squares estimation of the slope parameter.

3) The use of derivatives, e.g. up to the fourth order derivatives (A. Savitzky, M. J. E. Golay, Anal. Chem. 36, 1627–1639 (1964)). The derivative of the spectrum results in a transformed spectrum, consisting only of the relative changes between the adjacent wavelengths, and it has been shown that the peak intensities of derived spectra tend to be more linear with concentration (T. C. O'Haver, T. Begley, Anal. Chem. 53, 1876 (1981)).

4) The use of the Fourier transformation, or by use of the Standard Normal Variate transformation as disclosed in R. J. Barnes, M. S. Dhanoa and S. J. Lister, Appl. Spectrosc., Vol. 43, number 5, pp. 772–777 (1989).

(I.c) Data Analysis

Data analysis using chemometric techniques then allows the calibration model to be developed. There are several chemometric techniques which can be used, such as Principal Component Analysis (PCA), Partial Least Squares Regression (PLS), Principal Components Regression (PCR), Multilinear Regression Analysis (MLR) and Discriminant Analysis. The preferred chemometric technique according to the invention is the PLS method.

(I.c.1) Principal Component Analysis (PCA)

By PCA, a set of correlated variables is compressed into a smaller set of uncorrelated variables.

This transformation consists of a rotation of the coordinate system, resulting in the alignment of information on a fewer number of axes than in the original arrangement. Hereby, the variables that are highly correlated with one another will be treated as a single entity. By using PCA, it thus will be possible to obtain a small set of uncorrelated variables still representing most of the information which was present in the original set of variables, but being far easier to use in models.

In general, 2 to 15 principal components will account for 85% to 98% of the variance of the variables.

(I.c.2) Partial Least Squares Regression (PLS)

PLS is a modelling and computational method by which quantitative relations can be established between blocks of variables, e.g. a block of descriptor data (spectrum) for a series of samples and a block of response data measured on these samples. By the quantitative relation between the blocks, it is possible to enter spectral data for a new sample to the descriptor block and make predictions of the expected responses. One great advantage of the method is that the results can be evaluated graphically, by different plots. In most cases, visual interpretations of the plot are sufficient to obtain a good understanding of different relations between the variables. The method is based upon projections, similar to PCA. The PLS method is detailedly disclosed in Carlsson R., Design and optimization in organic synthesis, B. G. M. Vandeginste, O. M. Kvalheim, Eds., Data handling in science and technology (Elsevier, 1992), vol. 8.

(I.c.3) Principal Components Regression (PCR)

PCR is closely related to PCA and PLS. As in PLS, each object in the descriptor block is projected onto a lower dimensional space yielding in scores and loadings. The scores are then regressed against the response block in a least squares procedure leading to a regression model which can be used to predict unknown samples. The same model statistics as in PLS and PCA can be used to validate the model.

For an excellent tutorial in PCA, PLS and PCR, see P. Geladi et al in "Partial Least-Squares Regression: A Tutorial" in Anal. Chim. Acta, 185, 1–32 (1986), which is incorporated herein by reference in its entirety.

(I.c.4) Multilinear Regression Analysis (MLR)

By MLR, the best fitting plane for the property studied as a function of the spectra is defined, using least squares techniques to define each boundary of the plane. This plane then is used to recognize and assign a predicted value to an unknown property.

This technique is generally limited to relatively 'clean' systems where there is not a significant amount of matrix interference and, in contrast to PLS, it requires more objects than variables.

(I.c.5) Discriminant Analysis

This is a method whereby, by use of spectral data, the known property values are grouped into different clusters, separated by linear decision boundaries.

From its spectrum, a sample of unknown property value then can be matched to a cluster, and the property can be assigned a value, e.g. the average value of the cluster.

This is a very useful technique for quality screening, but requires a very large data base to obtain statistically significant results.

(II) DETERMINATION OF THE UNKNOWN PROPERTIES BY APPLICATION OF THE CALIBRATION MODEL

Once a calibration model has been developed, the determination of the unknown property can be performed by registering the absorption, reflectance or emission spectrum, in correspondence to (I.a). The processing of the thereby obtained spectral raw data as according to (I.b); optionally performing a data analysis on the processed spectral data as according to (I.c); and applying the developed calibration model to the thereby obtained data.

The invention will now be illustrated by way of examples.

EXAMPLE

Diffuse reflectance near-infrared spectrometry (NIRR) of the paper sample, linearization of spectral data and multivariate data evaluation using the PLS-algorithm were used to determine one or several of the physical properties selected from dry tensile strength, hydrophobicity, debonding energy, bursting strength, wettability and printability.

EXAMPLES OF DEVELOPMENT OF A CALIBRATION MODEL (A) Development of Learning Sets

SAMPLES

The reference samples of fluff for determination of wettability (FIG. 1), burst index (FIG. 2) and debonding energy (FIG. 3) consisted of in total 60 paper sheets of different pulp qualities of bleached sulphate pulp. Different amounts of debonding agents (quaternary fatty amines and amine oxides) had been added to the pulp.

The samples were scanned by NIRR and models developed.

Paper samples sized with AKD were produced at an experimental paper machine with the following experimental parameters Pulp: bleached hardwood 30%, 35% Birch and 35% Beech, pH=8.3–8.5, 80% pulp and 20% filler $CaCO_3$, 34° SR, resulting in 49 samples.
Chemicals: AKD, added amount 0 to 0.2% dry weight on dry fiber, starch 0.5% and anionic retention aid 0.5%
Addition order: AKD, starch and retention aid
Temperature: 20° C.
Grammage: 70 g/m²
Machine: system closed
Press section: 1) 4 bar, 2) 1 bar
Drying section: 60°/80°/95°/110° C.
Tests: Cobb and HST, off machine (om.) Cobb and HST after curing (c.) 30' 100° C.

All the samples were scanned with the NIRR instrument. A model was developed based on the known values for Cobb and HST. (See FIG. 4 and Table I.)

TABLE I

| DES-CRIPTOR | R^2 | SEP | MSEP | RMSEP | #PC:S | RSDb (%) | RSDw (%) |
|---|---|---|---|---|---|---|---|
| Cobb om. | 0.793 | 1.810 | 3.167 | 1.780 | 7 | 3.71 | 2.20 |
| Cobb c. | 0.781 | 2.014 | 3.938 | 1.985 | 6 | 2.86 | 2.89 |
| HST om. | 0.926 | 49.54 | 2385 | 48.83 | 10 | 5.21 | 4.70 |
| HST c. | 0.785 | 29.18 | 821.0 | 28.66 | 10 | 4.11 | 2.48 |

Paper samples sized with rosin were produced at an experimental paper machine with the following experimental parameters.

Pulp: bleached hardwood 30%, 35% Birch and 35% Beech, 2% alum., $H_2SO_4$, pH=4.5, resulting in 31 samples.
Chemicals: Rosin dispersion added amount 0 to 1,0% dry weight on dry fiber
Addition order: alum, rosin
Temperature: 20° C.
Grammage: 70 g/m²
Machine: system closed.
Press sect.: 1) 4 bar, 2) 1 bar
Drying section: 60/80/95/110
Tests: Cobb and HST off machine The paper samples treated with rosin and evaluated for Cobb and HST were scanned with a NIRR-instrument and models were developed (see Table II).

TABLE II

| DES-CRIPTOR | R^2 | SEP | MSEP | RMSEP | #PC:S | RSDb (%) | RSDw (%) |
|---|---|---|---|---|---|---|---|
| HST | 0.976 | 16.91 | 277.0 | 16.63 | 10 | — | 3.54 |
| Cobb | 0.961 | 0.599 | 0.344 | 0.586 | 9 | — | 4.20 |

Paper samples (45) of bleached sulphate intended for printing with ink-yet were tested for monochrome % area and colour % area, resp. and models were developed. (See FIG. 5 and 6.)

Paper samples containing UF-resin were produced at an experimental paper machine with the following experimental parameters:
Pulp: unbleached hardwood, sulphate, 32° SR
Chemicals: UF-resin, added amount 0 to 3% dry weight on dry fibre and alum 1,5%, pH=4,5 ($H_2SO_4$.), resulting in 51 samples
Temperature: 20° C.
Grammage:
  70 g/m²
Machine: system closed.
Press sect.: 1) 4 bar, 2) 1 bar
Drying section: 60°/80°/95°/110° C.

The 51 samples were tested for dry tensile strength and a model was developed and can be seen in Table III.

TABLE III

Statistical parameters from calibration of spectra scanned off machine (o.m) and after curing (c.)

| DES-CRIPTOR | R^2 | SEP | MSEP | RMSEP | #PC:S | RSDb (%) | RSDw (%) |
|---|---|---|---|---|---|---|---|
| Dry tensile strength - o-m. | 0.666 | 3.113 | 9.487 | 3.080 | 10 | 2.02 | 0.25 |
| Dry tensile strength - c. | 0.763 | 3.157 | 9.964 | 3.157 | 4 | 9.18 (1.41) | 0.73 |

NEAR INFRARED REFLECTANCE (NIRR) MEASUREMENTS

The NIRR measurements were obtained using a NIR Systems® 6500 spectrometer, from NIR systems, U.S., equipped with a High fat/moisture cell with a scan surface of up to 60 cm², with a spectral operating range between 400 nm and 2500 nm, in even intervals of 2 nm, yielding 1050 measurements at different wavelengths. Diffuse reflectance data were obtained as apparent absorbance, and transferred to a Macintosh® Quadra 700 computer.

(B) Data Processing

The spectral data matrix was reduced to the NIR region (1100–2500 nm) for greater modelling speed. The spectra were reduced by a factor of 8 (every eighth wavelength was kept), which resulted in 175 spectral points for modelling.

LINEARISING TRANSFORMATION

The best linearising function was established using a factorial design approach (R. J. O. Olsson, in Near Infra-Red Spectroscopy, I. T. Hildum, K. L. Naes T. and Tandberg A., Eds. Ellis Horwood Limited, Chichester, (1992) pp.

103–107) and was found to be the MSC with mean spectrum subtraction and incorporating the calculated intercept and slope parameters in the independent dataset (spectra).

The Mean Squared Error Prediction (MSEP) (H. Martens, T. Naes, Appl. Spect. 39, 491–500 (1985)) according to Eq. 3 herein below was evaluated as a number of latent variables kept in the PLS model. The linearising function/functions that yielded the smallest MSEP for the different descriptors then was used in the subsequent PLS modelling.

$$MSEP = \frac{1}{n} \sum_{i=1}^{n} (\hat{c}_i - c_i)^2 \quad (3)$$

n is the number of samples, $\hat{c}_i$ is the modelled descriptor value and $c_i$ is the traditionally measured descriptor value. The index i is the descriptor of the sample i.

(Other statistical parameters related to MSEP are the Standard Error Prediction (SEP) and the Root Mean Squared Error Prediction (RMSEP), given herein below by Eqs. 4 and 5, respectively.)

(C) Data Analysis

The MATLAB software V 3.5 was used for numerical calculations. The PLS-algorithm used for modelling the relationships between the spectra and descriptors is a customised function in the commercially available 'Chemometrics Toolbox' based on the NIPALS algorithm (H. Wold, P. Krishnaiah, Multivariate Analysis, 391 (1966)). The convergence criteria for the algorithm were $1 \times 10^{-10}$ or 100 iterations. The method of establishing the significant number of PLS-components was crossvalidation (S. Wold, Technometrics 20, 397–405 (1978)) (Jack-knifing) with one sample left out. This number here was found to be 15 for both the bleached and the unbleached paper samples. The values of the properties as defined above were mean-centered and scaled to unit variance prior to modelling (autoscaling or z-transform) and rescaled prior to model evaluation.

RESULTS

The measured vs. modelled values of the properties tensile strength, hydrophobicity, debonding energy, bursting strength, wettability and printability of the different paper qualities are plotted in FIGS. 1 to 6, respectively, with a 95% t-test confidence interval for the, to the data, least squares fitted line and shown in Tables I to III, respectively.

Accordingly, FIG. 1 represents the measured vs. predicted values of wettability in seconds of 60 samples of paper.

Figure 2:
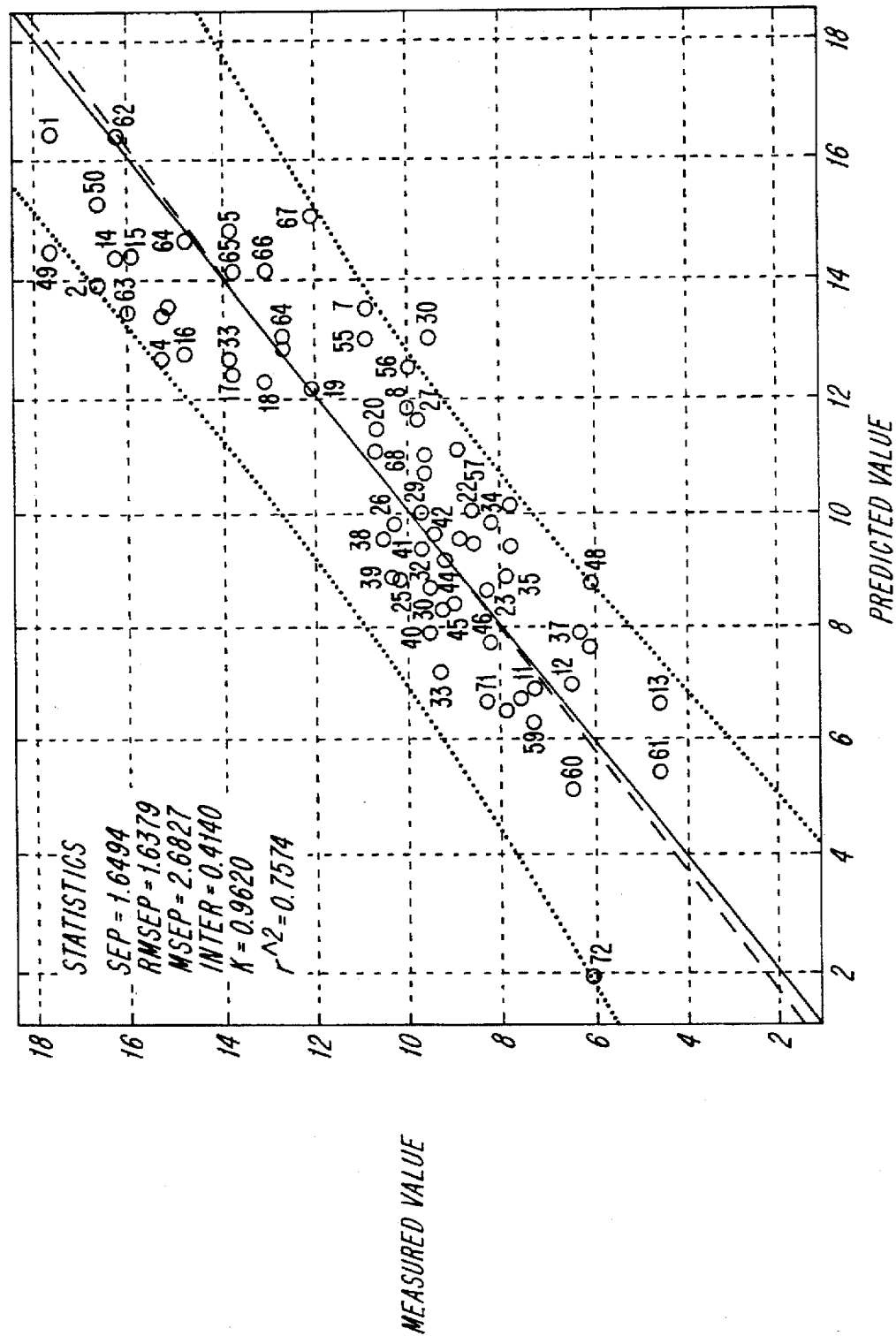
FIG. 2 represents the measured vs. predicted values of bursting strength as burst index in kPa*m$^2$/g of 60 samples of paper.
Figure 3:
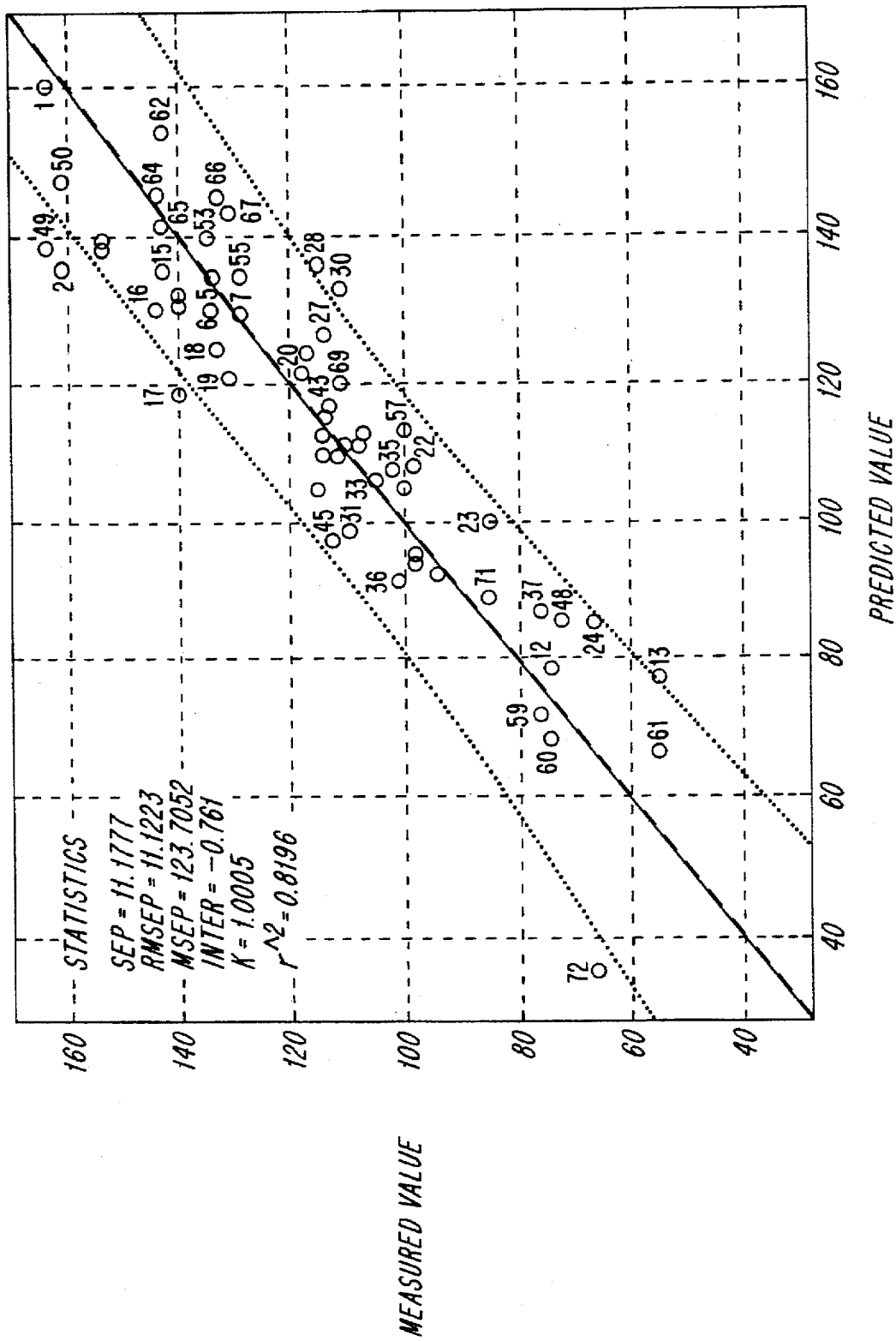
FIG. 3 represents the measured vs. predicted values of debonding energy in kgJoule/kg of 60 samples of paper.
Figure 4:
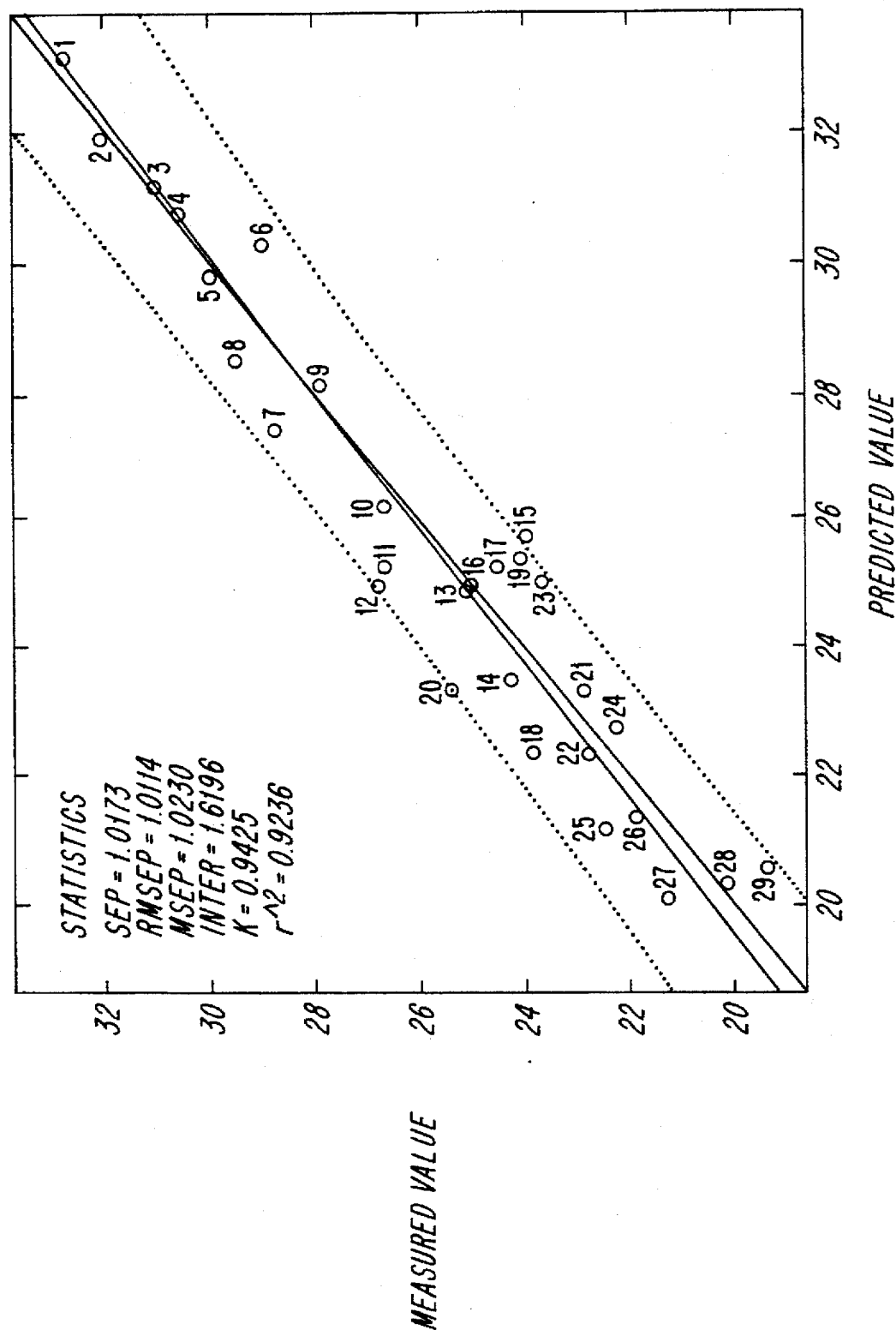
FIG. 4 represents the measured vs. predicted hydrophobicity according to Cobb off machine by measuring 49 samples of bleached paper.
Figure 5:
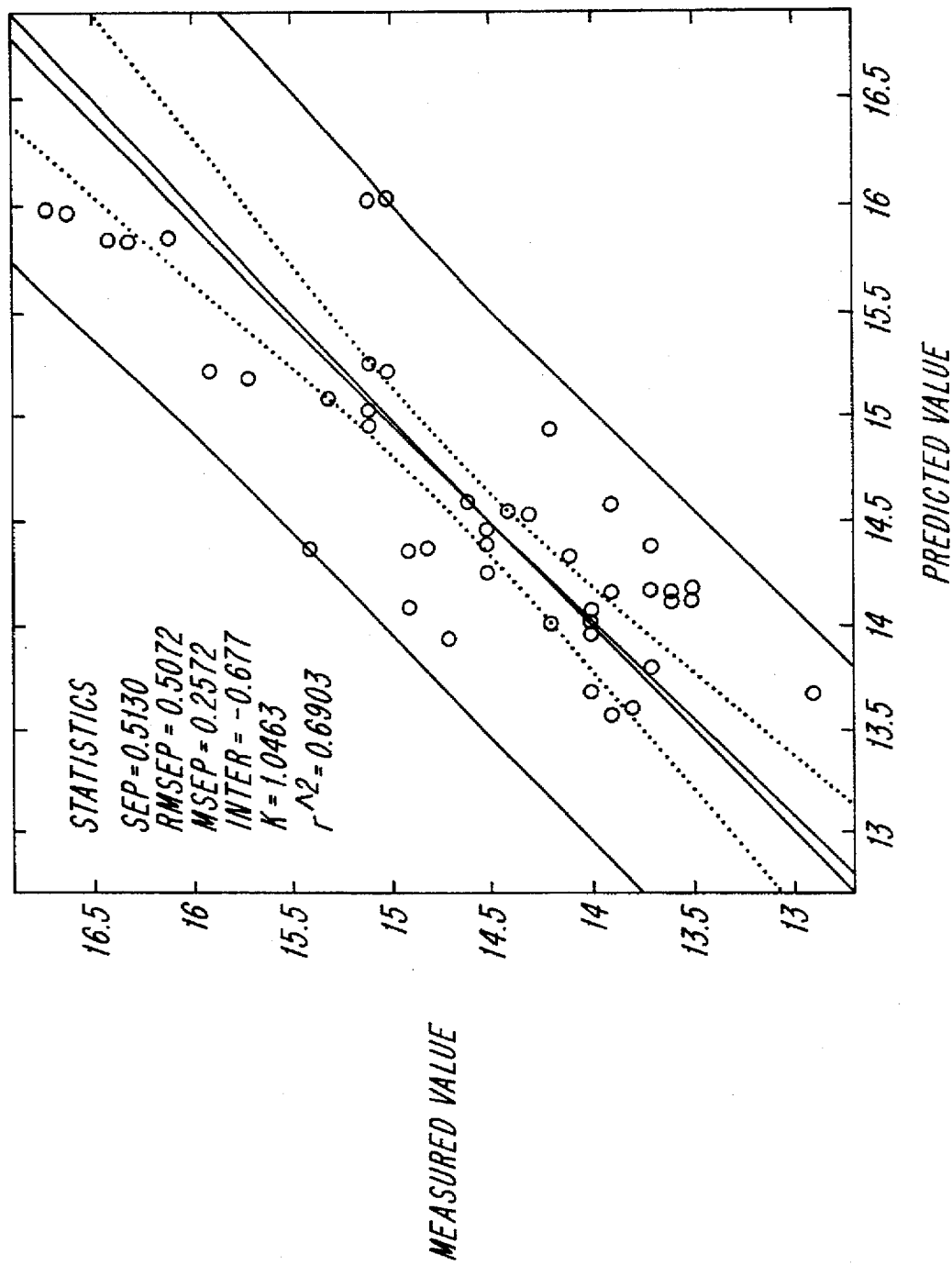
FIG. 5 represents the measured monochrome % area of 45 samples of bleached sulphate paper.
Figure 6:
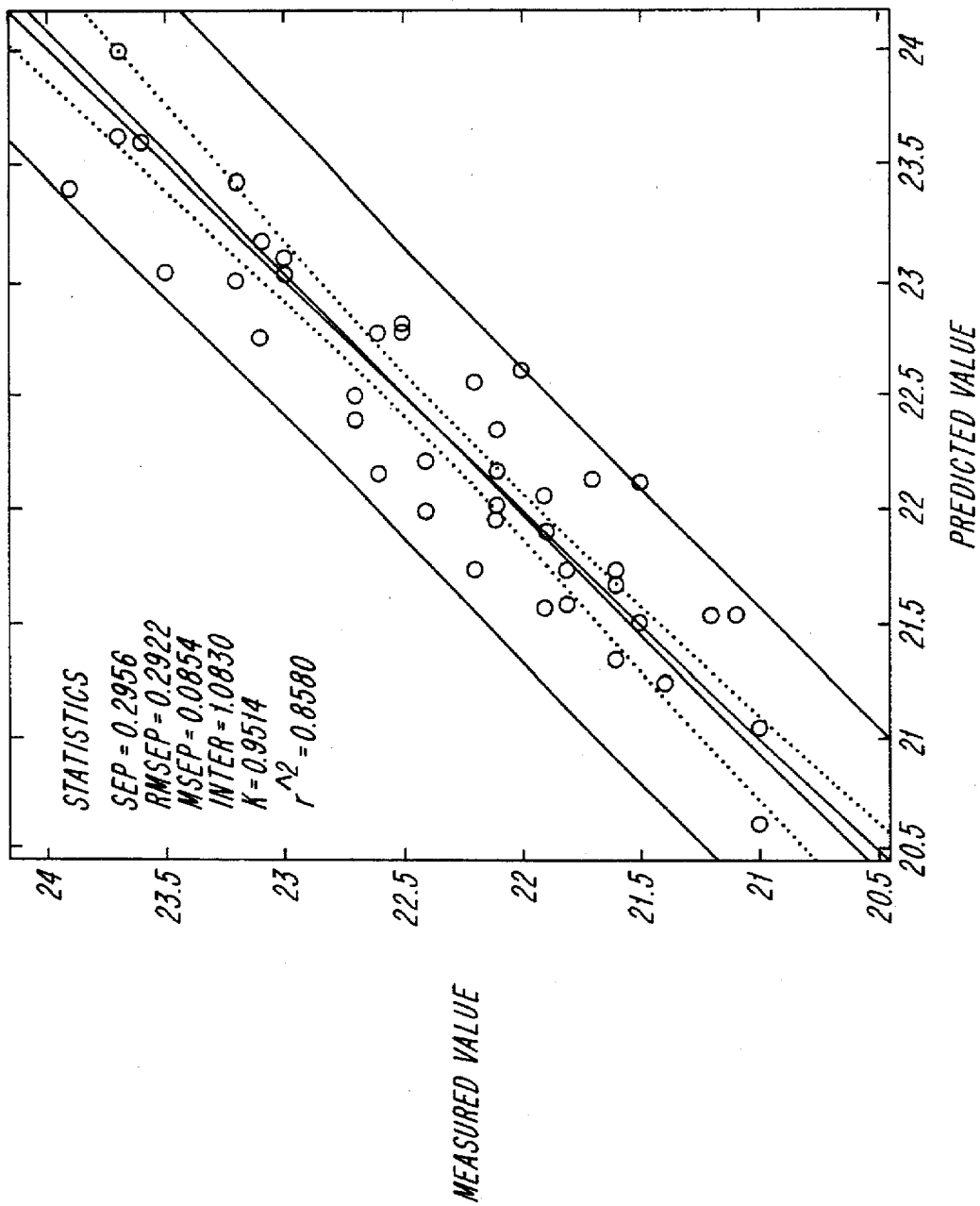
FIG. 6 represents the measured color % area of 45 samples of bleached sulphate paper.

FIG. 2 represents the measured vs. predicted values of bursting strength as burst index in kPa*m²/g of 60 samples of paper;

FIG. 3 represents the measured vs. predicted values of debonding energy in kgJoule/kg of 60 samples of paper; and FIG. 4 represents the measured vs. predicted hydrophobicity according to Cobb off machine by measuring 49 samples of bleached paper;

FIG. 5 represents the measured monochrome % area of 45 samples of bleached sulphate paper;

FIG. 6 represents the measured colour % area of 45 samples of bleached sulphate paper;

In the above mentioned figures and tables are also specified the unadjusted correlation coefficient ($r^2$), SEP (in kNm/kg) (Eq. 4, herein below), RMSEP (in kNm/kg) (Eq. 5, herein below), MSEP (in kN²m²/kg²), the intercept (INTER) and the slope (K) of the curves.

$$SEP = \sqrt{(n-1)^{-1} \sum_{i=1}^{n} (\hat{c}_i - c_i - \overline{(c - c)})^2} \quad (4)$$

$$RMSEP = \sqrt{MSEP} \quad (5)$$

(In Eq. 4, n, ĉ, c, and i respectively have the same meaning as in Eq. 3).

SEP is a good approximation of one standard deviation of the model residue.

Ideally, $r^2$ and k should be as close to 1 as possible; while SEP, RMSEP, MSEP, and the intercept should be as close to 0 as possible. In view of the values obtained, it will be possible to realize the very good validity and preciseness of the model.

Definitions of the statistical terms as used are given below.

| Symbols | |
|---|---|
| $y_i$ | Scalar y value for the i t:h sample i.e. the true reference analytical results. |
| $\hat{y}_i$ | The estimated $y_i$ value given by the PLS modelling. |
| $\bar{y}$ | Mean of $y_i$ values. |
| N | The total number of samples used for modelling. |

$r^2$ Correlation coefficient $$r^2 = \left( \frac{\sum_{i=1}^{N} (\hat{y}_i - \bar{y})^2}{\sum_{i=1}^{N} (y_i - \bar{y})^2} \right)$$

$r^2$ determines how well the data are adjusted to the least squares fitted straight line. Thus $r^2=1.00$ indicates that the calibration equation models 100% of the variation within the set of data. If $r^2=0.00$. then there is no correlation.

SEP Standard Error of Prediction $$SEP = \sqrt{\frac{\sum_{n=1}^{N} (\hat{y}_i - y_i - \overline{(\hat{y} - y)})^2}{(N-1)}}$$

SEP is a characterisation of the variance attributable to random unexplainable error.

MSEP Mean Square Error of Prediction $$MSEP = \frac{\sum_{n=1}^{N} (y_i - \hat{y}_i)^2}{N}$$

MSEP is the average squared differences between actual and predicted values. i.e. for a set of objects not present in the calibration. In the literature MSEP is also referred to as PRESS (Predicted Residual Error Sum of Squares)

RMSEP Root Mean Square Error of Prediction.

$$RMSEP = \sqrt{MSEP}$$

Transforms the MSEP into the original measured unit.

The advantage of the novel method of determining one or several of the physical properties tensile strength, hydrophobicity, debonding energy, bursting strength, wettability and printability in pulp and paper using chemometrics thus should be readily apparent. Indeed, a wide variety of properties may be analysed using the same calibration set. The invention thus provides a method whereby the quantifying of the properties of pulp and paper during production process can be performed in a very rapid and precise way on any type of pulp and paper.

We claim:

1. A method for quantifying one or more physical properties of fluff pulp or paper treated with paper chemicals, which method comprises
   (I) developing a calibration model by
     (I.a) registering absorption, reflectance or emission spectral raw data of reference samples of paper of known properties to develop a learning set;
     (I.b) processing the spectral raw data to reduce noise and adjust for drift and diffuse light scatter;
     (I.c) performing a data analysis by applying chemometric techniques to the processed learning sets; and
   (II) registering absorption, reflectance or emission spectral raw data of a sample of paper or fluff pulp having unknown properties; processing the spectral raw data as according to (I.b); and applying the developed calibration model on the processed spectral data in order to determine the unknown properties.

2. A method according to claim 1, wherein the recording of the absorption, reflectance or emission spectral raw data is performed in the wavelength of 200 nm to 400 µm.

3. A method according to claim 1, wherein the spectral data processing is performed using the Kubelka-Munk transform:

$$A_{ik} = \frac{(1-R_{ik})^2}{2R_{ik}} \quad (1)$$

wherein $R_{ik}$ is the apparent absorbance at the wavelength k, $A_{ik}$ is the transformed absorbance at the wavelength k, and the index i represents the sample spectra available.

4. A method according to claim 1, wherein the spectral data processing is performed using the Multiplicative Scatter Correction:

$$A_{ik} = \frac{R_{ik} - \hat{a}_i}{\hat{b}_i} \quad (2)$$

wherein $R_{ik}$ is the apparent absorbance at the wavelength k, $A_{ik}$ is the transformed absorbance at the wavelength k, $\hat{a}_i$ is the least squares estimation of the intercept parameter, and $\hat{b}_i$ is the least squares estimation of the slope parameter, the index i representing the sample spectra available, and the index k representing the available wavelengths.

5. A method according to claim 1, wherein the spectral data processing is performed by use of the Fourier transformation.

6. A method according to claim 1, wherein the spectral data processing is performed by use of up to the fourth order derivatives.

7. A method according to claim 1, wherein the spectral data processing is performed by use of the Standard Normal Variate transformation.

8. A method of quality screening the properties of a paper using the method according to claim 1, wherein the data analysis is performed by the Discriminant Analysis.

9. A method according to claim 1, wherein the data analysis is performed by the use of the Multilinear Regression Analysis technique.

10. A method according to claim 1, wherein the data analysis is performed by the use of the Principal Component Analysis technique.

11. A method according to claim 1, wherein the the data analysis is performed by the use of the Principal Components Regression technique.

12. A method according to claim 1, wherein the the data analysis is performed by the use of the Partial Least Squares technique.

13. A method according to claim 1 for quantification of dry tensile strength.

14. A method according to claim 1 for quantification of hydrophobicity.

15. A method according to claim 1 for quantification of bursting strength and index.

16. A method according to claim 1 for quantification of debonding energy.

17. A method according to claim 1 for quantification of wettability.

18. A method according to claim 1 for quantification of printability.

19. A method for maintaining a process control program wherein the properties of a paper are quantified to detect any change thereof and provide control input, in order to assure optimum dosage levels for chemical additives, by the use of a method as defined in claim 1.

20. A method according to claim 1, wherein a data analysis of the process spectral data obtained from the fluff pulp or paper of the unknown property is performed by the use of the Multilinear Regression Analysis technique.

21. A method according to claim 1, wherein a data analysis of the processed spectral data obtained from the fluff pulp or paper of the unknown property is performed by the use of the Principal Component Analysis technique.

22. A method according to claim 1, wherein a data analysis of the processed spectral data obtained from the fluff pulp or paper of the unknown property is performed by the use of the Principal Components Regression technique.

23. A method according to claim 1, wherein a data analysis of the process spectral data obtained from the fluff pulp or paper of the unknown property is performed by the use of the Partial Least Squares technique.

24. A method according to claim 2, wherein the recording of the absorption, reflectance or emission spectral raw data is performed in the wavelength of 800 nm to 2500 nm.

25. A method according to claim 1, wherein one or more physical properties of paper containing wet strength agents, dry strength agents, starches, retention agents, sizing agents, or debonding agents are quantified.

26. A method according to claim 1, wherein the physical properties are selected from the group consisting of wet strength, dry tensile strength, hydrophobicity, debonding energy, bursting strength, wettability and printability.

27. A method according to claim 1, wherein the physical properties are selected from the group consisting of dry tensile strength, hydrophobicity, debonding energy, bursting strength, wettability and printability.

28. A method according to claim 1, wherein (I.c) the processed spectral data of the reference samples are transferred into latent variables based on principal component analysis, and chemometric techniques applied on the latent variables in order to find the mathematical expression of the calibration model; and that in (II) the processed spectral data are transferred into latent variables as according to (I.c), and the developed calibration model applied on the latent variables in order to determine the unknown properties.

* * * * *